US008455550B2

(12) United States Patent
Cuisiat et al.

(10) Patent No.: US 8,455,550 B2
(45) Date of Patent: Jun. 4, 2013

(54) DERIVATIVES OF AMINOCYCLOBUTANE OR AMINOCYCLOBUTENE, THEIR METHOD OF PREPARATION AND THEIR USE AS MEDICAL PRODUCTS

(75) Inventors: Stéphane Cuisiat, Castres (FR); Adrian Newman-Tancredi, Castres (FR); Olivier Vitton, Castres (FR); Bernard Vacher, Castres (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 0 days.

(21) Appl. No.: 13/258,546

(22) PCT Filed: Apr. 2, 2010

(86) PCT No.: PCT/EP2010/054452
§ 371 (c)(1),
(2), (4) Date: Nov. 9, 2011

(87) PCT Pub. No.: WO2010/112597
PCT Pub. Date: Oct. 7, 2010

(65) Prior Publication Data
US 2012/0029013 A1 Feb. 2, 2012

Related U.S. Application Data

(60) Provisional application No. 61/246,446, filed on Sep. 28, 2009.

(30) Foreign Application Priority Data

Apr. 3, 2009 (FR) .................................... 09 52196

(51) Int. Cl.
*A61K 31/165* (2006.01)
*A61P 25/00* (2006.01)
*C07C 237/24* (2006.01)

(52) U.S. Cl.
USPC .......................... 514/620; 564/163; 564/161

(58) Field of Classification Search
None
See application file for complete search history.

(56) References Cited

U.S. PATENT DOCUMENTS

| 5,621,142 A | 4/1997 | Mochizuki et al. |
| 6,992,110 B2 | 1/2006 | Kranzler et al. |
| 2004/0019116 A1 | 1/2004 | Kranzler et al. |
| 2009/0098085 A1 | 4/2009 | Sun et al. |

FOREIGN PATENT DOCUMENTS

| WO | WO 95/22521 A1 | 8/1995 |
| WO | WO 03/039598 A1 | 5/2003 |
| WO | WO 2004/039320 A2 | 5/2004 |
| WO | WO 2006/138264 A2 | 12/2006 |
| WO | WO 2009/105887 A1 | 9/2009 |

OTHER PUBLICATIONS

Allan et al. Neurochemical Research 1980, 5 (4), 393-400.*
Allan et al. Journal of Neurochemistry 1980, 34 (3), 652-654.*
Aitken et al., "Pyrolysis of Tricyclic Cyclobutane-Fused Sulfolanes as a Route to cis-1,2-divinyl Compounds and Their Cope-Derived Products", J. Chem. Soc. Perkin Trans., vol. 1, 1999, pp. 605-614.
Avila et al., "1-Phenyl-2t-(2-hydroxy-2-propyl)-1r-cyclobutanecarboxamide($^1$)", Journal of Chemical Crystallography, vol. 27, No. 2, 1997, pp. 125-128, XP009123351.
Bardin et al., "In the Formalin Model of Tonic Nociceptive Pain, 8-OH-DPAT Produces 5-HT1A Receptor-Mediated, Behaviorally Specific Analgesia", European Journal of Pharmacology, vol. 421, 2001, pp. 109-114.
Basler et al., "Conformationally Constrained β-Amino Acid Derivatives by Intramolecular [2+2]-Photocycloaddition of a Tetronic Acid Amide and Subsequent Lactone Ring Opening", J. Org. Chem., vol. 70, 2005, pp. 9798-9808.
Bonnaud et al., "1-Aryl-2-(aminomethyl) cyclopropanecarboxylic Acid Derivatives. A New Series of Potential Antidepressants", J. Med. Chem., vol. 30, 1987, pp. 318-325.
Chen et al., "Studies on the SAR and Pharmacophore of Milnacipran Derivatives as Monoamine Transporter Inhibitors", Bioorganic & Medicinal Chemistry Letters, vol. 18, 2008, pp. 1346-1349.
Chen et al., "Triple Uptake Inhibitors: Therapeutic Potential in Depression and Beyond", Expert Opinion on Investigational Drugs, vol. 16, No. 9, 2007, pp. 1365-1377.
Dyck et al., "Characterization of Thien-2-yl 1S,2R-Milnacipran Analogues as Potent Norepinephrine/Serotonin Transporter Inhibitors for the Treatment of Neuropathic Pain", J. Med. Chem., vol. 51, No. 22, Oct. 28, 2008, pp. 7265-7272.
Ebmeier et al., "Recent Developments and Current Controversies in Depression", Lancet, vol. 367, Jan. 14, 2006, p. 153-167.
International Search Report, dated May 20, 2010, for Appilcation No. PCT/EP2010/054452.
Kaiser et al., "Asterane, XVII: Ober die Synthese von [4] Propellanderivaten des Tetraasterans", Chem. Ber. vol. 118, No. 6, 1985, pp. 2266-2281.
Kawamoto et al., "2(7H)-Oxepinones: Photochemical Oxidation of 6-Monosubstituted Fulvenes", Chemistry Letters, 1972, pp. 807-810.
Kazuta et al., "Synthesis of (1S,2R)-1-Phenyl-2-[(S)-1-aminopropyl]-N, N-diethylcyclopropanecarboxamide (PPDC) Derivatives Modified at the Carbamoyl Moiety As a New Class of NMDA Receptor Antagonists", Bioorg. & Med. Chem., vol. 10, 2002, pp. 1777-1791.

(Continued)

*Primary Examiner* — Sreeni Padmanabhan
*Assistant Examiner* — Irina Neagu
(74) *Attorney, Agent, or Firm* — Birch, Stewart, Kolasch & Birch, LLP

(57) ABSTRACT

The present invention concerns compounds of general formula (1), where in:—-a- is a single or double bond, Ar is an aromatic group, substituted or unsubstituted, R1 and R2 each independently or together are: a hydrogen atom or $C_1$-$C_6$ alkyl group, branched or unbranched, saturated or unsaturated, substituted or unsubstituted; the groups R1 and R2 may also form a heterocycle, R3 and R3' each independently or together are a hydrogen atom or $C_1$-$C_6$ alkyl group, X is an oxygen atom or a sulphur atom, and the addition salts of the compounds of general formula (1) with pharmaceutically acceptable mineral acids or organic acids.

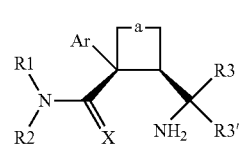

(1)

17 Claims, 1 Drawing Sheet

OTHER PUBLICATIONS

Kazuta et al., "Synthesis of Derivatives of (1S,2R)-1-Phenyl-2-[(S)-1-aminopropyl] -N N-diethylcyclopropanecarboxamide (PPDC) Modified at the 1-Aromatic Moiety as Novel NMDA Receptor Antagonists: The Aromatic Group is Essential . . . ", Bioorg. & Med. Chem., vol. 10, 2002, pp. 3829-3848.

Kosugi et al., "Photochemical Cycloaddition Reactions of α, β-Unsaturated Lactones with Olefins, and Application to Synthesis of Natural Products", Bulletin of the Chemical Society of Japan, vol. 49, No. 2, 1976, pp. 520-528.

Malpass et al. "Modification of 1-Substituents in the 2-Azabicyclo[2.1.1]hexane Ring System; Approaches to Potential Nicotinic Acetylcholine Receptor Ligands from 2,4-Methanoproline Derivatives", J. Org. Chem., vol. 68, 2003, pp. 9348-9355.

O'Donnell et al., "(±)-trans-2-(Aminomethyl)cyclobutanecarboxylic Acid Hydrochloride: A Rigid Analogue of γ-Aminobutyric Acid", J. Med. Chem., vol. 23, 1980, pp. 1142-1144.

Ohmori et al., "A Method for Designing Conformationally Restricted Analogues Based on Allylic Strain: Synthesis of a Novel Class of Noncompetitive NMDA Receptor Antagonists Having the Acrylamide Structure", J. Med. Chem., vol. 46, 2003, pp. 5326-5333.

O'Malley et al., "Total Synthesis of Dimeric Pyrrole—Imidazole Alkaloids: Sceptrin, Ageliferin, Nagelamide E, Oxysceptrin, Nakamuric Acid, and the Axinellamine Carbon Skeleton", J. AM. Chem. Soc., vol. 129, 2007, p. 4762-4775.

Ono et al., "Conformational Analysis of the NMDA Receptor Antagonist (1S,2R)-1-Phenyl-2-[(S)-1-aminopropyl]-N,N-diethylcyclopropanecarboxamide (PPDC) Designed by a Novel Conformational Restriction Method Based on the Structural . . . ", Chem. Pharm. Bull., vol. 50, No. 7, 2002, pp. 966-968.

Pang et al., "Differential Inhibitory Effects of Melatonin Analogs and Three Naphthalenic Ligands on 2-[125I]iodomelatonin Binding to Chicken Tissues", Journal of Pineal Research, vol. 23, 1997, pp. 148-155.

Perez et al., "Design and Synthesis of New Potent, Silent 5-HT1A Antagonists by Covalent Coupling of Aminopropanol Derivatives with Selective Serotonin Reuptake Inhibitors", Bioorganic & Medicinal Chemistry Letters, vol. 8, 1998, pp. 3423-3428.

Polshettiwar et al., "Thionation of Carbonyl Compounds Using Phosphorus Pentasulfide and Hexamethyldisiloxane under Microwave Irradiations", Journal of Chemical Research, Jul. 2004, pp. 474-476.

Roggen et al., "Synthesis of Enantiomerically Pure Milnacipran Analogs and Inhibition of Dopamine, Serotonin, and Norepinephrine Transporters", Bioorganic & Medicinal Chemistry Letters, vol. 17, 2007, pp. 2834-2837.

Rush et al., "Bupropion-SR, Sertraline, or Venlafaxine-XR after Failure of SSRIs for Depression", The New England Journal of Medicine, vol. 354, No. 12, Mar. 23, 2006, p. 1231-1242.

Shuto et al., "(±)-(Z)-2-(Aminomethyl)-1-phenylcyclopropanecarboxamide Derivatives as a New Prototype of NMDA Receptor Antagonists", J. Med. Chem., vol. 38, 1995, pp. 2964-2968.

Shuto et al., "Conformational Restriction by Repulsion Between Adjacent Substituents on a Cyclopropane Ring: Design and Enantioselective Synthesis of 1-Phenyl-2-(1-aminoalkyl)-N N-diethylcyclopropanecarboxamides as Potent NMDA . . . ", J. Org. Chem., vol. 61, 1996, pp. 915-923.

Shuto et al., "Synthesis and Biological Activity of Conformationally Restricted Analogs of Milnacipran: (1S,2R)-1-Phenyl-2[(S)-1-aminopropyl]-N,N-diethylcyclopropanecarboxamide, an Efficient Non-competitive N-Methyl-D-aspartic Acid Receptor . . . ", J. Med. Chem., 1996, vol. 39, pp. 4844-4852.

Shuto et al., "Synthesis and Biological Activity of Conformationally Restricted Analogues of Milnacipran: (1S, 2R)-1-2-[(R)-1-amino-2-propynyl]-N,N-diethylcyclopropanecarboxamide Is a Novel Class of NMDA Receptor Channel Blocker", J. Med. Chem., vol. 41, 1998, pp. 3507-3514.

Tamiya et al., "Identification of 1S,2R-Milnacipran Analogs as Potent Norepinephrine and Serotonin Transporter Inhibitors", Bioorganic & Medicinal Chemistry Letters, vol. 18, 2008, pp. 3328-3332.

Vickers et al., "Studies on a Series of Milnacipran Analogs Containing a Heteroaromatic Group as Potent Norepinephrine and Serotonin Transporter Inhibitors", Bioorganic & Medicinal Chemistry Letters, vol. 18, 2008, pp. 3230-3235.

Yamaguchi et al., "Synthesis of 1-Arylpiperazyl-2-Phenylcycloprapanes Designed as Antidopaminergic Agents: Cyclopropane-Based Conformationally Restricted analogs of Haloperidol", Bioorganic & Medicinal Chemistry, vol. 16, 2008, pp. 8875-8881.

Zirvi, "The Biochemorphology of Cyclobutanecarboximides Part II", Pakistan Journal of Scientific and Industrial Research, vol. 16, Nos. 3-4, Jun.-Aug. 1973, pp. 107-109.

* cited by examiner

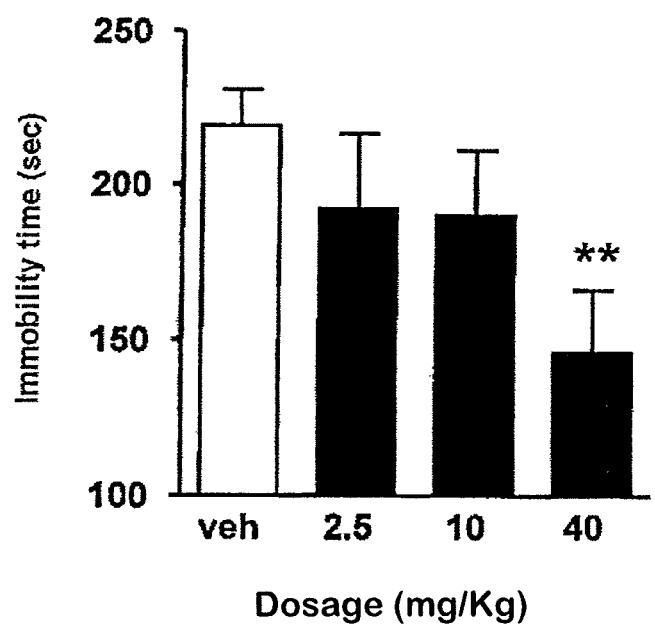

DERIVATIVES OF AMINOCYCLOBUTANE OR AMINOCYCLOBUTENE, THEIR METHOD OF PREPARATION AND THEIR USE AS MEDICAL PRODUCTS

The present invention concerns novel derivatives of aminocyclobutane or aminocyclobutene, their method of preparation, pharmaceutical compositions containing the same and their use as medicinal products.

The prior art is represented by milnacipran (cis-(±)-N,N-diethyl-(1-phenyl-2-aminomethyl)-cyclopropanecarboxamide: Merck Index, 12th Edition, N° 6281) which meets the following formula:

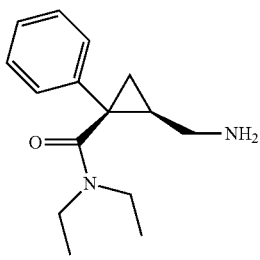 [SMILES: CCN(CC)C(=O)[C@@]1(c2ccccc2)C[C@H]1CN]

it is used in numerous countries to treat depression (CNS Drugs 2008, 22, 587) and is approved in the United States for the treatment of fibromyalgia syndrome. Also, in U.S. Pat. No. 6,992,110 and WO 2003039598 (Cypress Bioscience, Inc.) milnacipran is also claimed for its use in the treatment of pain and chronic fatigue syndrome.

Since the discovery of milnacipran, numerous analogs thereof have been described in the literature. Globally, the derivatives under consideration meet the following generic formula:

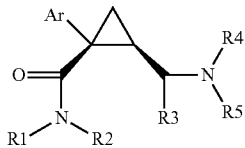

As examples of structural modifications made to the backbone of milnacipran, the following works can be cited: Bonnaud et al., J. Med. Chem. 1987, 30, 78; Asahi Kasei Kogyo K. K., WO 9522521; Shuto et al., J. Med. Chem. 1995, 38, 2964; Shuto et al., J. Med. Chem. 1996, 61, 915; Shuto et al., J. Med. Chem. 1996, 39, 4844; Shuto et al., J. Med. Chem. 1998, 41, 3507; Perez et al., Bioorg. Med. Chem. Lett., 1998, 8, 3423; Shuto et al., Bioorg. Med. Chem. 2002, 10, 1777; Shuto et al., Bioorg. Med. Chem. 2002, 10, 3829; Shuto et al., Chem. Pharm. Bull. 2002, 50, 966; Shuto et al., J. Med. Chem. 2003, 46, 5326; Collegium Pharmaceutical, Inc., WO 2004039320; Shuto et al., Biorg. Med. Chem. 2008, 16, 8875; Hansen et al., Biorg. Med. Chem. Lett. 2007, 17, 2834; Chen et al., Biorg. Med. Chem. Lett. 2008, 18, 1346; Chen et al., Biorg. Med. Chem. Lett. 2008, 18, 3230; Chen et al., Biorg. Med. Chem. Lett. 2008, 18, 3328; Chen et al., J. Med. Chem. 2008, 51, 7265.

Like milnacipran, these derivatives generally behave as multiple inhibitors of monoamine reuptake sites (Expert Opin. Investig. Drugs 2007, 16, 1365); the relative activity of the products under consideration at the different sites varies in relation to the type of the Ar and R1-R5 groups.

From a structural viewpoint, the compounds of the invention differ from milnacipran, and its derivative products, through the size of the carbon cycle and the possible incorporation of a double bond in this cycle. These structural modifications have major repercussions on the pharmacological activity of the products of the invention. On this account, the formula (I) compounds set themselves apart from milnacipran and its derivative compounds, not only through their chemical structure but also through their pharmacological properties.

The compounds of the present invention are of general formula (1):

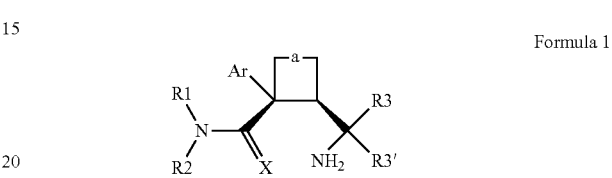

Formula 1 wherein:
-a- is a single or double bond
Ar is an aromatic group, substituted or unsubstituted,
R1 and R2 each independently or together are:
   a hydrogen atom or a $C_1$-$C_6$ alkyl group, branched or unbranched, saturated or unsaturated, substituted or unsubstituted; the R1 and R2 groups may also form a heterocycle,
R3 and R3' each independently or together are a hydrogen atom or a $C_1$-$C_6$ alkyl group;
X is an oxygen atom or a sulphur atom.

The term $C_1$-$C_6$ <<alkyl>> designates aliphatic, linear or branched, saturated or unsaturated hydrocarbon chains, and comprising the specified number of carbon atoms, for example the methyl, ethyl, propyl, butyl, pentyl or hexyl.

The term $C_1$-$C_6$ <<alkoxy>> designates a linear or branched hydrocarbon chain containing 1 to 6 carbon atoms and an oxygen atom, for example a methoxy radical, an ethoxy radical, a propoxy radical, a butoxy radical, a pentoxy radical or a hexoxy radical.

The term <<halogen>> designates a fluorine, chlorine, bromine or iodine.

The term <<Aromatic>> designates:
an aromatic hydrocarbon which may be monocyclic, such as phenyl for example, or bicyclic such as naphtyl for example,
or a heteroaromatic radical which corresponds to an aromatic hydrocarbon such as defined previously, in which one or more carbon atoms have been substituted by a heteroatom such as nitrogen for example or oxygen or sulphur, those which may be cited including pyridine, pyrimidine, imidazole, indole, furane or thiophene for example and in particular thiophene-2-yl, thiophen-3-yl and pyridin-3-yl.

The term <<heterocycle>> designates either a stable monocycle containing 5 to 7 atoms, or a stable bicycle containing 8 to 11 atoms, possibly being either saturated or unsaturated and consisting of carbon atoms and of one to four heteroatoms chosen from among nitrogen, oxygen, sulphur and containing at least one nitrogen atom. Also included in the definition of bicycle are the monocyclic heterocycles fused with a benzene core. As examples mention may be made of pyrrolidine, indoline and tetrahydroisoquinoline.

The term <<pharmaceutically acceptable salts>> for example designates: fumarate, maleate, hydrochloride and all other salts recommended in: Handbook of Pharmaceutical Salts, Properties, Selection and Use; Stahl, P. H., Wermuth, C. G. Eds.; Wiley-VCH, 2002.

According to one embodiment of the invention, if the aromatic group Ar is substituted in the compounds of general formula (1), the substituent(s) are: one or more halogen atoms, or one or more $C_1$-$C_6$ alkyl groups, or one or more $C_1$-$C_6$ alcoxy groups, or a cyano group.

According to one embodiment of the invention, if the R1 and/or R2 group are a substituted $C_1$-$C_6$ alkyl group, the substituent is a halogen atom.

According to the invention, the formula (1) compounds are those in which Ar is:
  a phenyl group substituted or unsubstituted by one or more halogen atoms, or by one or more $C_1$-$C_6$ alkyl groups, or by one or more $C_1$-$C_6$ alcoxy groups, or by a cyano group,
  or a naphtyl group substituted or unsubstituted by one or more halogen atoms, or by one or more $C_1$-$C_6$ alkyl groups, or by one or more $C_1$-$C_6$ alcoxy groups, or by a cyano group,
  or a heteroaromatic group substituted or unsubstituted by one or more halogen atoms, or by one or more $C_1$-$C_6$ alkyl groups, or by one or more $C_1$-$C_6$ alcoxy groups, or by a cyano group.

According to one embodiment of the invention, the formula (1) compounds are those in which Ar is:
  a phenyl group substituted or unsubstituted by one or two halogen atoms, or by one or two methyl groups, or by one or two methoxy groups, or by a cyano group,
  or a naphtylene-2-yl group,
  or a heteroaromatic group chosen from the group consisting of: thiophene-2-yl, thiophen-3-yl and pyridin-3-yl.

According to the invention, the formula (1) compounds are those in which R1 and R2 each independently or together are:
  a $C_1$-$C_3$ alkyl group, branched or unbranched, saturated or unsaturated, optionally substituted by a fluorine atom,
  or a heterocycle chosen from the group consisting of: pyrrolidine, indoline, and tetrahydroisoquinoline.

Among the compounds of general formula (1) which come under the present invention, one appreciated class of compounds corresponds to the compounds of general formula (1) in which R3 and R3' together represent a hydrogen atom or independently a methyl or ethyl group and a hydrogen atom.

Among the compounds of general formula (1) which come under the present invention, one appreciated class of compounds corresponds to the compounds of general formula (1) in which X is an oxygen atom.

Among the compounds of general formula (1) which come under this invention, one class of compounds corresponds to the compounds of general formula (1) in which X is an oxygen atom and R3 and R3' are a hydrogen atom.

The invention also extends to the salts of the formula (I) compounds with pharmaceutically acceptable organic or mineral acids, and to the enantiomers of the formula (1) compounds. The invention also comprises the tautomeric forms of the compounds of general formula (1).

The compounds of the invention comprise at least two asymmetric carbon atoms and can therefore be obtained in the form of racemic mixtures or enantiomers. The invention not only concerns every pure enantiomer i.e. associated with less than 5% of the other enantiomer, but also the mixture of enantiomers in all proportions. The compounds of the invention can therefore be used as pure enantiomer or as racemic or non-racemic mixtures of enantiomers.

More specifically, the invention relates to the mixtures and to the pure enantiomers of the following products:

cis-N,N-Diethyl-(1-phenyl-2-aminomethyl)-cyclobutanecarboxamide
cis-N,N-Diethyl-(1-phenyl-2-aminomethyl)-cyclobutenecarboxamide
cis-N,N-Diethyl-(1-(thiophen-2-yl)-2-aminomethyl)-cyclobutanecarboxamide
cis-N,N-Diethyl-(1-(thiophen-3-yl)-2-aminomethyl)-cyclobutanecarboxamide
cis-N,N-Diethyl-(1-(pyridin-3-yl)-2-aminomethyl)-cyclobutanecarboxamide
cis-N,N-Diethyl-(1-(naphthalen-2-yl)-2-aminomethyl)-cyclobutanecarboxamide
cis-N,N-Diethyl-(1-(2-fluorophenyl)-2-aminomethyl)-cyclobutanecarboxamide
cis-N,N-Diethyl-(1-(2-cyanophenyl)-2-aminomethyl)-cyclobutanecarboxamide
cis-N,N-Diethyl-(1-(3-chlorophenyl)-2-aminomethyl)-cyclobutanecarboxamide
cis-N,N-Diethyl-(1-(3-fluorophenyl)-2-aminomethyl)-cyclobutanecarboxamide
cis-N,N-Diethyl-(1-(3-methoxyphenyl)-2-aminomethyl)-cyclobutanecarboxamide
cis-N,N-Diethyl-(1-(3-cyanophenyl)-2-aminomethyl)-cyclobutanecarboxamide
cis-N,N-Diethyl-(1-(3-methylphenyl)-2-aminomethyl)-cyclobutanecarboxamide
cis-N,N-Diethyl-(1-(3,4-dichlorophenyl)-2-aminomethyl)-cyclobutanecarboxamide
cis-N,N-Diethyl-(1-(3,4-difluorophenyl)-2-aminomethyl)-cyclobutanecarboxamide
cis-N,N-Diethyl-(1-(3,4-methylenedioxyphenyl)-2-aminomethyl)-cyclobutanecarboxamide
cis-1-Indolin-1-yl-(1-phenyl-2-aminomethyl)-cyclobutanecarboxamide
cis-1-Indolin-1-yl-(1-(3-chlorophenyl)-2-aminomethyl)-cyclobutanecarboxamide
cis-1-Tetrahydroquinolin-2-yl-(1-phenyl-2-aminomethyl)-cyclobutanecarboxamide
cis-1-Tetrahydroquinolin-2-yl-(1-(3-fluorophenyl)-2-aminomethyl)-cyclobutanecarboxamide
cis-1-Tetrahydroquinolin-2-yl-(1-(3-chlorophenyl)-2-aminomethyl)-cyclobutanecarboxamide
cis-1-Tetrahydroquinolin-2-yl-(1-(3-cyanophenyl)-2-aminomethyl)-cyclobutanecarboxamide
cis-1-Tetrahydroquinolin-2-yl-(1-(3-methylphenyl)-2-aminomethyl)-cyclobutanecarboxamide
cis-N,N-Diallyl-(1-phenyl-2-aminomethyl)-cyclobutanecarboxamide
cis-N,N-Diallyl-(1-(3-fluorophenyl)-2-aminomethyl)-cyclobutanecarboxamide
cis-N,N-Diallyl-(1-(3-chlorophenyl)-2-aminomethyl)-cyclobutanecarboxamide
cis-N,N-Diallyl-2-yl-(1-(3-cyanophenyl)-2-aminomethyl)-cyclobutanecarboxamide
cis-N,N-Diallyl-2-yl-(1-(3-methylphenyl)-2-aminomethyl)-cyclobutanecarboxamide
cis-N,N-Diethyl-(1-phenyl-2-aminoethyl)-cyclobutanecarboxamide
cis-N,N-Diethyl-(1-(3-chlorophenyl)-2-aminoethyl)-cyclobutanecarboxamide
cis-N,N-Diethyl-(1-phenyl-2-aminomethyl)-cyclobutanethiocarboxamide Method of Synthesis:

The invention also extends to the method to prepare derivatives of general formula (1).

The derivatives of general formula (1) can be obtained from a derivative of formula (2)

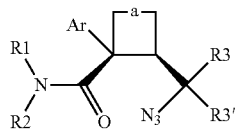

Formula 2

Applying a method similar to the method described in J. Org. Chem. 1996, 61, 915. In the compounds of formula (2, the groups Ar, R1, R2, R3, R3' and (-a-) have the same designation as for the derivative of formula (1).

The formula compound (2) can itself be prepared from a compound of formula (3):

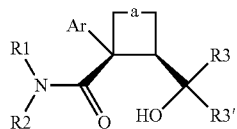

Formula 3 by applying a conventional method in organic chemistry such as described for example in: J. Med Chem. 1980, 23, 1142; Chem. Ber. 1985, 118, 2266; J. Org. Chem. 2003, 68, 9348; J. Am. Chem. Soc. 2007, 129, 4762. In the formula (3) compounds, the groups Ar, R1, R2, R3, R3' and (-a-) have the same designation as for the formula (1) compound.

The compound of formula (3) can in turn be synthesized from the lactone of formula (4).

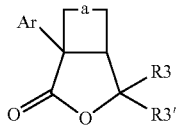

Formula 4 wherein Ar and (-a-) have the same designation as for the derivative of formula (1). The opening of the lactones by an amine is a reaction well known to persons skilled in the art and largely described in the literature: J. Chem. Soc. Perkin Trans. 1 1999, 605; J. Org. Chem. 2005, 70, 9798. The formula 4 compound in which Ar is a phenyl group and (-a-) represents a single bond is known [59664-87-8] and its preparation is reported in Bull. Chem. Soc. Jpn. 1976, 49, 520. The derivative of formula (4) in which Ar is a phenyl group and (-a-) represents a double bond is also known [38029-37-7] as is its preparation cf. Chem. Lett. 1972, 807 and Bull. Chem. Soc. Jpn. 1976, 49, 520. By analogy, the derivatives of formula (4) can be prepared by cycloaddition [2+2] using a conventional method in organic chemistry and well known to those skilled in the art.

The formula 1 compounds in which X=S can be prepared from the corresponding formula 1 compound with X=O by protection of the primary amine function then reaction with a thioanhydride following the method described in J. Chem. Res. 2004, 474.

One particular enantiomer of the formula (1) compounds can be obtained by resolution of the racemic mixture or of a mixture enriched with one of the enantiomers at the most appropriate step of the synthesis.

Another aspect of the invention comprises novel intermediates of synthesis which are used in the method to prepare the formula (1) compounds described above.

It notably concerns the synthesis intermediate of formula (2):

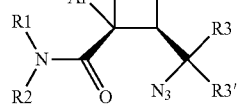

Formula 2 wherein (-a-), Ar, R1, R2, R3 and R3' are such as defined above, used for the preparation of compounds of general formula (1).

It also concerns the intermediate of formula (3):

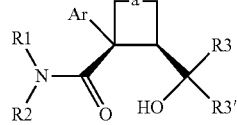

Formula 3 wherein (-a-), Ar, R1, R2, R3 and R3' are such as defined previously, used for the preparation of compounds of general formula (2).

EXAMPLES

The following examples illustrate but in no way limit the invention.

In the examples and reference examples below:

(i) the progression of the reactions is monitored by thin-layer chromatography TLC and therefore the reaction times are only mentioned by way of indication;

(ii) different crystalline shapes may give different melting points, the melting points reported in the present application are those of the products prepared following the described method and are not corrected;

(iii) the structure of the products obtained according to the invention is confirmed by the spectra of nuclear magnetic resonance NMR and centesimal analysis, the purity of the end products is verified by TLC, the enantiomeric purity of the reaction intermediates and of the end products is determined by chiral phase HPLC;

(iv) the NMR spectra are recorded in the indicated solvent. The chemical shifts ($\delta$) are expressed in parts per million (ppm) relative to tetramethylsilane. The multiplicity of signals is indicated by: s, singlet; d, doublet; t, triplet; q, quadruplet; m, multiplet; l, large;

(v) the different symbols of the units have their usual denotation: μg (microgram); mg (milligram); g (gram); mL (milliliter); mA (milliampere); ° C. (degree Celsius); mmole (millimole); nmole (nanomole); cm (centimeter); nm (nanometer); min (minute); s (second), Hz (hertz); [α] (specific rotation measured at 589 nm, 25° C. and at concentration c, in the present invention the dimension deg $cm^2 \, g^{-1}$ is always implied); pressures are given in millibars (mb);

(vi) the abbreviations have the following meaning: mp (melting point);

(vii) by "room temperature" is meant a temperature of between 20° C. and 25° C.

Example 1

(±)-cis-N,N-diethyl (1-phenyl-2-aminomethyl)-cyclobutanecarboxamide (1a)

Step 1: (±)-cis-N,N-diethyl (1-phenyl-2-hydroxymethyl)-cyclobutanecarboxamide (3a)

In a three-necked flask in an atmosphere of nitrogen, place 1.6 eq of diethylamine and THF. Cool the mixture to 0° C. and add 1.6 eq of BuLi dropwise. Agitate the mixture 5 min at 0° C. then cool to −78° C. Next, add lactone (1 eq) dropwise in solution in THF (final concentration relative to lactone=0.25 mol/L). Agitate the mixture at −78° C. for 2 h. Return to 5° C. followed by hydrolysis of the reaction medium with saturated $NH_4Cl$ solution. Dilute the reaction mixture with $H_2O$ then extract with ethyl acetate. Dry the organic phase over $MgSO_4$, filter and concentrate. Purify the residue by flash chromatography (eluent: Heptane/ethyl acetate, 1:1). The title product is obtained in the form of a yellow oil (yield=83%).

$^1$H NMR (CDCl$_3$, 400 MHz) δ: 0.66 (t, 3H), 1.07 (t, 3H), 1.54 (m, 1H), 2.14 (m, 1H), 2.59-2.71 (m, 3H), 2.80 (m, 1H), 2.99 (m, 1H), 3.21 (m, 1H), 3.35 (m, 1H), 3.62-3.68 (m, 1H), 3.92-3.95 (m, 1H), 5.26 (dd, 1H), 7.24 (m, 1H), 7.37 (t, 2H), 7.44 (d, 2H).

Step 2: (±)-cis-N,N-diethyl (1-phenyl-2-azidomethyl)-cyclobutanecarboxamide (2a)

Add 1 eq alcohol (2a) and DMF. Cool the mixture to 0° C. and add in the following order: 18 eq $NaN_3$, 3 eq $CBr_4$ and 3 eq $PPh_3$. Agitate the reaction mixture 5 min at 0° C. then return to room temperature. Agitate for 4 h then dilute the reaction medium with $H_2O$ and extract with ethyl acetate. Dry the organic phase over $MgSO_4$, filter and concentrate. Purify the residue by flash chromatography (eluent: Heptane/ethyl acetate, 9:1). The title product is obtained in the form of a colourless oil (yield=84%).

$^1$H NMR (CDCl$_2$, 400 MHz) δ: 0.36 (t, 3H), 1.09 (t, 3H), 1.70-1.77 (m, 1H), 2.03-2.09 (m, 1H), 2.19 (m, 1H), 2.78 (m, 1H), 2.90-3.03 (m, 2H), 3.09-3.19 (m, 2H), 3.44 (m, 1H), 3.63 (d, 2H), 7.23-7.26 (m, 1H), 7.34-7.39 (m, 4H).

Step 3: (±)-cis-N,N-diethyl (1-phenyl-2-aminomethyl)-cyclobutanecarboxamide (1a)

Add 1 eq azide (2a) and the methanol. Degas the solution for 30 min with nitrogen then add Pd/C (10 wt. %). Purge the system (empty cycle/$H_2$ gas) and hydrogenate the mixture under low hydrogen pressure for 3 h at room temperature under agitation. Purge the reaction medium with nitrogen, remove the catalyst by filtering and evaporate the solvent. The title compound is obtained in the form of a white powder (yield=70%).

$C_{26}H_{24}N_2O$
mp: 95° C.
$^1$H NMR (CDCl$_2$, 400 MHz) δ: 0.27 (t, 3H), 1.09 (t, 3H), 1.29 (s, 1H), 1.60-1.65 (m, 1H), 1.81-1.86 (m, 1H), 2.16 (c, 1H), 2.77 (m, 1H), 2.84-3.00 (m, 4H), 3.05 (m, 1H), 3.24 (q, 1H), 3.50 (m, 1H), 7.21-7.25 (m, 2H), 7.33-7.36 (m, 4H).
% Theoretical C, 73.91; H, 9.30; N, 10.78
% Found C, 73.95; H, 9.28; N, 10.75.

Salification of compound (1a) with oxalic acid leads to obtaining the oxalate of the title compound in the form of white crystals.
$C_{26}H_{24}N_2O \cdot C_2H_2O_4$
mp: 175° C.
$^1$H NMR (DMSO d$_6$, 400 MHz) δ: 0.33 (t, 3H), 0.97 (t, 3H), 1.70 (t, 1H), 1.98-2.04 (m, 2H), 2.76-3.04 (m, 7H), 3.33 (m, 1H), 7.27 (t, 1H), 7.35-7.43 (m, 4H).
% Theoretical C, 61.70; H, 7.48; N, 7.99
% Found C, 61.74; H, 7.56; N, 8.12.

Example 2

(+)-cis-N,N-diethyl (1-phenyl-2-aminomethyl)-cyclobutanecarboxamide (1a1)

The enantiomers of (±)-cis-N,N-diethyl (1-phenyl-2-aminomethyl)-cyclobutanecarboxamide (1a) are separated by chiral phase chromatography (Chiralpack IC) using as eluting solvent a mixture of acetonitrile-ethanol-butylamine (90:10:0.1).

(+)-cis-N,N-Diethyl (1-phenyl-2-aminomethyl)-cyclobutanecarboxamide (1a1), $[\alpha]_D$=+0.84°

Salification of compound (1a1) with oxalic acid leads to obtaining the oxalate of the title compound in the form of white crystals.
mp: 170° C.
$[\alpha]_D$=−22.7°.
$^1$H NMR (DMSO d$_6$, 400 MHz) δ: 044 (t, 3H), 0.98 (t, 3H), 1.68 (m, 1H), 2.08 (c, 1H), 2.31 (m, 1H), 2.76-2.92 (m, 4H), 2.98-3.10 (m, 2H), 3.15 (dd, 1H), 3.28-3.36 (m, 1H), 7.29 (t, 1H), 7.37-7.45 (m, 4H), 8.00 (s, 2H).
% Theoretical C, 61.70; H, 7.48; N, 7.99
% Found C, 61.85; H, 7.22; N, 7.77.

Example 3

(−)-cis-N,N-diethyl (1-phenyl-2-aminomethyl)-cyclobutanecarboxamide (1a2)

(−)-cis-N,N-Diethyl (1-phenyl-2-aminomethyl)-cyclobutanecarboxamide (1a1), $[\alpha]_D$=−0.84°

Salification of compound (1a1) with oxalic acid leads to obtaining the oxalate of the title compound in the form of white crystals.
mp: 170° C.
$[\alpha]_D$=+21.7°.
% Theoretical C, 61.70; H, 7.48; N, 7.99
% Found C, 60.62; H, 7.37; N, 7.83.

Example 4

(±)-cis-1-indolinyl-(1-phenyl-2-aminomethyl)-cyclobutanecarboxamide (1b)

Step 1: (±)-cis-1-indolinyl-(1-phenyl-2-hydroxymethyl)-cyclobutanecarbo-xamide (3b)

This compound is obtained following the same experimental conditions as those used for the synthesis of intermediate (3a) replacing diethylamine with indoline. The title compound (3b) is obtained after crystallization in isopropyl ether (yield=52%).

$^1$H NMR (CDCl$_3$, 400 MHz) δ: 1.57-1.14 (m, 1H), 2.21 (m, 1H), 2.66-2.94 (m, 4H), 3.45 (m, 1H), 3.62 (m, 1H), 3.69 (dd, 1H), 4.07 (dd, 1H), 4.76 (s, 2H), 7.02 (t, 1H), 7.12 (d, 1H), 7.22 (t, 1H), 7.24-7.29 (m, 1H), 7.39 (t, 2H), 7.51 (d, 2H), 8.27 (d, 1H).

Step 2: (±)-1-indolinyl-(1-phenyl-2-azidomethyl)-cyclobutanecarboxamide (2b)

Following the same experimental conditions as those used for synthesis of intermediate (2a), the title compound (2b) is obtained after purification by flash chromatography (eluent: heptane/ethyl acetate, 95:5); yield=99%.

$^1$H NMR (CDCl$_3$, 400 MHz) δ: 1.77-1.84 (m, 1H), 2.17-2.31 (m, 2H), 2.81-2.88 (m, 1H), 2.91-2.99 (m, 1H), 3.03-3.06 (m, 1H), 3.12-3.21 (m, 2H), 3.45 (m, 1H), 3.77 (d, 2H), 7.01 (t, 1H), 7.11 (d, 1H), 7.22 (t, 1H), 7.26-7.29 (m, 1H), 7.36 (m, 4H), 8.28 (d, 1H).

Step 3: (±)-1-indolinyl-(1-phenyl-2-aminomethyl)-cyclobutanecarboxamide (1b)

Following the same experimental conditions as those used for the synthesis of compound (1a), the title compound (1b) is obtained after purification by flash chromatography. Salification of compound (1b) with fumaric acid leads to obtaining the fumarate of the title compound in the form of white crystals.

$C_{20}H_{22}N_2O.C_4H_4O_4$
mp: 156° C.

$^1$H NMR (400 MHz, d$_6$ DMSO): 1.75 (t, J=11.2 Hz, 1H), 2.09 (dt, J=19.6, 8.8 Hz, 1H), 2.24 (t, J=11.2 Hz, 1H), 2.87-3.09 (m, 6 Hz), 3.22 (dd, J=12, 4.4 Hz, 1H), 3.27 (dt, J=9.6, 9.2 Hz, 1H), 3.41-3.48 (m, 2H), 6.4 (s, 2H), 7.00 (t, J=7.6 Hz, 1H), 7.16 (t, J=7.2 Hz, 2H), 7.31 (t, J=6.8 Hz, 1H), 7.41-7.47 (m, 4H), 8.14 (d, J=8.4 Hz, 1H).

% Theoretical C, 68.23; H, 6.20; N, 6.63
% Found C, 68.05; H, 6.41; N, 6.64.

Example 5

(±)-cis-1-tetrahydroquinolin-2-yl-(1-phenyl-2-aminomethyl)-cyclobutanecarboxamide (1c)

Following the same experimental conditions as those used for the synthesis of compound (1a), the title compound (1c) is obtained. Salification of compound (1c) with fumaric acid leads to obtaining the fumarate of the title compound in the form of white crystals.

$C_{21}H_{24}N_2O.C_4H_4O_4$
mp: 159° C.

$^1$H NMR (400 MHz, d$_6$ DMSO): 1.71-1.74 (m, 1H), 2.04-2.18 (m, 2H), 2.29-2.39 (m, 1H), 2.85 (m, 1 Hz), 2.95-3.11 (m, 3H), 3.1-3.2 (m, 2H), 3.19 (m, 1H), 3.6-3.71 (m, 2H), 4.08 (s, 1H), 4.41 (d, J=17.2 Hz, 1H), 4.79 (d, J=17.6 Hz, 1H), 6.42 (s, 2H), 6.97 (d, J=7.6 Hz, 1H), 7.08 (d, J=7.2 Hz, 1H), 7.11-7.16 (m, 2H), 7.29-7.33 (m, 2H), 7.41-7.434 (m, 3H).

% Theoretical C, 68.79; H, 6.47; N, 6.42
% Found C, 68.57; H, 6.48; N, 6.46.

Example 6

(±)-cis-N-ethyl-(1-phenyl-2-aminomethyl)-cyclobutanecarboxamide (1d)

Applying the same experimental conditions as those used for the synthesis of compound (1a), the title compound (1d) is obtained. Salification of compound (1c) with fumaric acid leads to obtaining the hemifumarate of the title compound in the form of white crystals.

$C_{24}H_{20}N_2O.C_2H_2O_2$
mp: 174° C.

$^1$H NMR (400 MHz, d$_6$ DMSO): 0.95 (t, J=6.8 Hz, 3H), 1.68 (dt, J=18.4, 9 Hz, 1H), 1.97-2.03 (m, 1H), 2.21-2.24 (m, 1H), 2.69-2.75 (m, 1H), 2.80-2.83 (m, 1H), 2.96 (t, J=7.6 Hz, 1H), 3.04 (dd, J=14, 6.8 Hz, 2H), 3.19-3.22 (m, 1H), 6.37 (s, 1H), 7.22 (dd, J=8.4, 4.4 Hz, 1H), 7.32-7.34 (m, 3H), 7.79 (s, 1H).

% Theoretical C, 66.18; H, 7.55; N, 9.65
% Found C, 65.74; H, 7.56; N, 9.21.

Example 7

(±)-cis-N,N-diallyl (1-phenyl-2-aminomethyl)-cyclobutanecarboxamide (1e)

Applying the same experimental conditions as those used for compound (1a), the title compound (1e) is obtained. Salification of compound (1c) with fumaric acid leads to obtaining the fumarate of the title compound in the form of white crystals.

$C_{28}H_{24}N_2O.C_4H_4O_4$
mp: 95° C.

$^1$H NMR (400 MHz, d$_6$ DMSO): 1.68-1.73 (m, 1H), 2.04 (dt, J=19.6, 8.8 Hz, 1H), 2.19-2.24 (m, 1H), 2.88 (dd, J=20.4, 9.2 Hz, 1H), 2.99 (t, J=12 Hz, 1H), 3.13 (dd, J=12.4, 5.6 Hz, 1H), 3.31 (dd, J=16, 6.8 Hz, 1H), 3.46-3.56 (m, 2H), 4.01 (dd, J=15.2, 5.2 Hz, 1H), 4.75-4.85 (m, 1H), 4.92-4.97 (m, 3H), 5.06 (d, J=10.4 Hz, 1H), 5.60-5.70 (m, 1H), 6.42 (s, 2H), 7.27-7.32 (m, 1H), 7.38-7.44 (m, 4H).

% Theoretical C, 65.98; H, 7.05; N, 7.00
% Found C, 66.28; H, 6.91; N, 6.89.

Example 8

(±)-cis-N,N-diethyl (1-(thiophen-2-yl)-2-aminomethyl)-cyclobutanecarboxamide (1f)

Following the same experimental conditions as those used for the synthesis of compound (1a), the title compound (1f) is obtained. Salification of compound (1c) with fumaric acid leads to obtaining the fumarate of the title compound in the form of white crystals.

$C_{24}H_{22}N_2OS.C_4H_4O_4$
mp: 140° C.

$^1$H NMR (400 MHz, d$_6$ DMSO): 0.59 (t, J=6.4 Hz, 3H), 0.99 (t, J=6.8 Hz, 3H), 1.74 (t, J=10.4 Hz, 1H), 2.11-2.20 (m, 2H), 2.86-3.13 (m, 7H), 3.31-3.45 (m, 1H), 6.45 (s, 2H), 7.03 (d, J=4.4 Hz, 1H), 7.06 (m, 1H), 7.45 (d, J=5.2 Hz, 1H).

% Theoretical C, 56.53; H, 6.85; N, 7.32; S, 8.38
% Found C, 56.46; H, 6.81; N, 7.22; S, 8.05.

Example 9

(±)-cis-N,N-diethyl (1-(thiophen-3-yl)-2-aminomethyl)-cyclobutanecarboxamide (1g)

Applying the same experimental conditions as those used for the synthesis of compound (1a), the title compound (1g) is obtained. Salification of compound (1c) with fumaric acid leads to obtaining the fumarate of the title compound in the form of white crystals.

$C_{24}H_{22}N_2OS.C_4H_4O_4$
mp: 159° C.

$^1$H NMR (400 MHz, d$_6$ DMSO): 0.49 (t, J=6.4 Hz, 3H), 0.98 (t, J=6.8 Hz, 3H), 1.69 (t, J=10.4 Hz, 1H), 2.06-2.14 (m, 2H), 2.83-3.18 (m, 7H), 3.31-3.45 (m, 1H), 6.46 (s, 2H), 6.93 (d, J=4.8 Hz, 1H), 7.48 (s, 1H), 7.56 (dd, J=4.4, 2.8 Hz, 1H).

% Theoretical C, 56.33; H, 6.85; N, 7.32; S, 8.38
% Found C, 56.72; H, 6.86; N, 7.43; S, 8.34.

Example 10

(±)-cis-N,N-diethyl (1-(2-chlorophenyl)-2-aminomethyl)-cyclobutanecarboxamide (1h)

Applying the same experimental conditions as those used for the synthesis of compound (1a), the title compound (1h) is obtained. Salification of compound (1c) with fumaric acid leads to obtaining the fumarate of the title compound in the form of white crystals.

$C_{26}H_{23}ClN_2O \cdot C_4H_4O_4$
mp: 170° C.
$^1$H NMR (400 MHz, $d_6$ DMSO): 0.07 (t, J=6.8 Hz, 3H), 1.02 (t, J=7.2 Hz, 3H), 1.75-1.85 (m, 2H), 1.97 (dt, J=9.2, 7.6 Hz, 1H), 2.67-2.83 (m, 2H), 2.91-3.06 (m, 3H), 3.22-3.45 (m, 3H), 6.48 (s, 2H), 7.32 (t, J=7.2 Hz, 1H), 7.42-7.47 (m, 2H), 7.75 (d, J=7.6 Hz, 1H).
% Theoretical C, 56.35; H, 6.23; N, 5.97
% Found C, 57.61; H, 6.35; N, 6.26.

Example 11

-cis-N,N-Diethyl-(1-(3-chlorophenyl)-2-(1-aminoethyl))-cyclobutanecarboxamide

Applying the same experimental conditions as those used for the synthesis of compound (1a), the title compound (1i) is obtained. Salification of compound (1c) with fumaric acid leads to obtaining the fumarate of the title compound in the form of white crystals.

$C_{26}H_{23}ClN_2O \cdot C_4H_4O_4$
mp: 160° C.
$^1$H NMR (400 MHz, $d_6$ DMSO): 0.44 (t, J=6.8 Hz, 3H), 0.98 (t, J=6.8 Hz, 3H) 1.69 (t, J=10 Hz, 1H), 2.04 (dt, J=18.1 Hz, 1H), 2.13-2.17 (m, 1H), 2.78-2.86 (m, 2H), 2.89-2.93 (m, 3H), 3.02-3.08 (m, 2H), 3.3-3.37 (m, 1H), 6.43 (s, 2H), 7.34-7.38 (m, 3H), 7.46 (t, J=8.4 Hz, 1H).
% Theoretical C, 58.46; H, 6.62; N, 6.82
% Found C, 59.04; H, 6.60; N, 6.73.

Example 12

(±)-cis-N,N-diethyl (1-(4-fluorophenyl)-2-aminomethyl)-cyclobutanecarboxamide (1j)

Applying the same experimental conditions as those used for the synthesis of compound (1a), the title compound (1j) is obtained. Salification of compound (1c) with fumaric acid leads to obtaining the di-fumarate of the title compound in the form of white crystals.

$C_{26}H_{23}FN_2O \cdot C_8H_8O_8$
mp: 183° C.
$^1$H NMR (400 MHz, $d_6$ DMSO): 0.46 (t, J=6.8 Hz, 3H), 0.97 (t, J=6.8 Hz, 3H), 1.66-1.71 (m, 1H), 2.08 (dt, J=17.6, 6.4 Hz, 1H), 2.08-2.1 (m, 1H), 2.75-2.88 (m, 4H), 2.96-3.16 (m, 2H), 3.14 (dd, J=12.4, 5.6 Hz, 1H), 3.28-3.45 (m, 1H), 6.57 (s, 4H), 7.25 (t, J=8.8 Hz, 2H), 7.41 (dd, J=8.4, 5.2 Hz, 2H).
% Theoretical C, 56.47; H, 6.12; N, 5.49
% Found C, 56.61; H, 6.81; N, 7.29.

Example 13

(±)-cis-N,N-diethyl (1-(2,3-dichlorophenyl)-2-aminomethyl)-cyclobutanecarboxamide (1k)

Applying the same experimental conditions as those used for the synthesis of compound (1a), the title compound (1k) is obtained. Salification of compound (1c) with fumaric acid leads to obtaining the fumarate of the title compound in the form of white crystals.

$C_{26}H_{22}Cl_2N_2O \cdot C_4H_4O_4$
mp: 184° C.
$^1$H NMR (400 MHz, $d_6$ DMSO): 0.09 (t, J=6.8 Hz, 3H), 1.02 (t, J=6.8 Hz, 3H), 1.76-1.84 (m, 2H), 1.98-2.02 (m, 1H), 2.67-2.78 (m, 2H), 2.90-3.05 (m, 3H), 3.22-3.39 (m, 3H), 6.45 (s, 2H), 7.47 (t, J=8 Hz, 1H), 7.60 (d, J=8 Hz, 1H), 7.77 (d, J=8 Hz, 1H).
% Theoretical C, 53.94; H, 5.88; N, 6.29
% Found C, 54.28; H, 5.85; N, 6.24.

Example 14

(±)-cis-N,N-diethyl (1-(3,4-dichlorophenyl)-2-aminomethyl)-cyclobutanecarboxamide (1l)

Applying the same experimental conditions as those used for the synthesis of compound (1a), the title compound (1l) is obtained. Salification of compound (1c) with fumaric acid leads to obtaining the fumarate of the title compound in the form of white crystals.

$C_{26}H_{22}Cl_2N_2O \cdot C_4H_4O_4$
mp: 182° C.
$^1$H NMR (400 MHz, $d_6$ DMSO): 0.51 (t, J=6.4 Hz, 3H), 0.97 (t, J=7.2 Hz, 3H), 1.67 (t, J=10 Hz, 1H), 1.99-2.07 (m, 1H), 2.21 (t, J=8.8 Hz, 1H), 2.78-2.95 (m, 5H), 3.03-3.11 (m, 3H), 3.33-3.37 (m, 2H), 6.43 (s, 2H), 7.36 (d, J=8.4 Hz, 1H), 7.59 (s, 1H), 7.69 (d, J=8.41 Hz, 1H).
% Theoretical C, 53.94; H, 5.88; N, 6.29
% Found C, 54.05; H, 5.90; N, 6.17.

Example 15

(±)-cis-N,N-diethyl (1-(3-methoxyphenyl)-2-aminomethyl)-cyclobutanecarboxamide (1m)

Applying the same experimental conditions as those used for the synthesis of compound (1a), the title compound (1m) is obtained. Salification of compound (1c) with fumaric acid leads to obtaining the fumarate of the title compound in the form of white crystals.

$C_{27}H_{26}N_2O_2 \cdot C_4H_4O_4$
mp: 130° C.
$^1$H NMR (400 MHz, $d_6$ DMSO): 0.43 (t, J=6.8 Hz, 3H), 0.98 (t, J=6.8 Hz, 3H), 1.70 (t, J=9.6 Hz, 1H), 2.05 (t, J=8.4 Hz, 1H), 2.08-2.14 (m, 1H), 2.68-2.82 (m, 1H), 2.86-3.09 (m, 6H), 3.29-3.38 (m, 1H), 3.76 (s, 3H), 6.48 (s, 2H), 6.89 (s, 2H), 6.93 (d, J=7.6 Hz, 1H), 7.33 (t, J=8.4 Hz, 1H).
% Theoretical C, 62.05; H, 7.44; N, 6.89
% Found C, 61.77; H, 7.23; N, 6.71.

Example 16

(±)-cis-N,N-diethyl (1-(3,4-methylenedioxyphenyl)-2-aminomethyl)-cyclobutanecarboxamide (1n)

Applying the same experimental conditions as those used for the synthesis of compound (1a), the title compound (1n) is obtained. Salification of compound (1c) with fumaric acid leads to obtaining the fumarate of the title compound in the form of white crystals.

$C_{27}H_{24}N_2O_3 \cdot C_4H_4O_4$
mp: 197° C.
$^1$H NMR (400 MHz, $d_6$ DMSO): 0.51 (t, J=6.8 Hz, 3H), 0.97 (t, J=6.8 Hz, 3H), 1.66 (t, J=10 Hz 1H), 1.99 (dt, J=18, 8.8 Hz, 1H), 2.10-2.14 (m, 1H), 2.80-2.87 (m, 5H), 2.99-3.10 (m, 2H), 3.32-3.45 (m, 1H), 6.0 (s, 2H), 6.44 (s, 2H), 6.84-6.88 (m, 2H), 6.94 (d, J=7.6 Hz, 1H).

% Theoretical C, 59.99; H, 6.71; N, 6.66
% Found C, 60.00; H, 6.76; N, 6.59.

Example 17

-cis-N,N-Diethyl-(1-(1-phenyl)-2-(1-aminoethyl))-cyclobutanecarboxamide

Applying the same experimental conditions as those used for the synthesis of compound (1a), the title compound (1o) is obtained. Salification of compound (1c) with fumaric acid leads to obtaining the fumarate of the title compound in the form of white crystals.

$C_{27}H_{26}N_2O \cdot C_4H_4O_4$
mp: 178° C.
$^1$H NMR (400 MHz, $d_6$ DMSO): 0.51 (t, J=6.8 Hz, 3H), 0.99 (t, J=6.8 Hz, 3H), 1.00 (m, 1H), 1.15 (d, J=7.2 Hz, 3H), 1.78-1.80 (m, 1H), 2.06 (dt, J=21.2, 9.2 Hz, 1H), 2.49-2.51 (m, 1H), 2.74-2.80 (m, 3H), 2.88-2.96 (m, 1H), 3.06-3.13 (m, 1H), 3.30-3.39 (m, 1H), 3.59 (dt, J=6.8 Hz, 1H), 6.40 (s, 2H), 7.28 (t, J=6.8 Hz, 1H), 7.41-7.45 (m, 4H).

% Theoretical C, 64.60; H, 7.74; N, 7.17
% Found C, 64.66; H, 7.67; N, 7.02.

Biological Tests:
1) Evaluation of Analgesic Activity:

The analgesic activity of the formula (1) compounds and of milnacipran, chosen as reference compound, was determined using a conventional pain module in which formaldehyde is injected to cause a painful sensation in animals (Eur. J. Pharmacol. 2001, 421, 109).

Protocol:

The rats (Male Sprague Dawley rats (ICO: OFA SD [IOPS], Iffa Credo, France) are placed in observation boxes in Plexiglas above an angled mirror to facilitate observation of their hind paws. After thirty minutes habituation, the animals are given an injection of formaldehyde diluted to 2.5% on the plantar surface of the right hind paw. The injection of formaldehyde produces behavioural responses which occur in two phases:

an early phase, 0 to 5 min after injection of formaldehyde, corresponding to stimulation of the receptors specialized in the transmission of nociceptive stimuli.

a late phase which occurs between 20 and 30 min after injection. This phase corresponds to the stimulation of receptors by inflammatory mediators and/or to hyperexcitability of the dorsal horn induced during the first phase. This later phase therefore involves central sensitization and causes pain more representative of neuropathic pain compared with the pain which occurs during the first phase. On this account, only the results obtained in this later phase are taken into consideration in the present application.

To study the compounds of the invention, we selected two expressions of painful behaviour (paw licking, lifting of injected paw) and chose as observation period the period which corresponds to the late phase (i.e. 22.5-27.5 min). During this 5 min phase, the animals are observed every 30 s and the following behaviours are recorded: licking or non-licking of the injected hind paw and lifting or not of the injected hind paw. Ten observations give a maximum score of 10 for each parameter. The products of the invention are given via intra-peritoneal route 15 min before the injection of formaldehyde.

Results:

In the formaldehyde test, the formula (1a) compound representing the compounds of the invention has remarkable analgesic activity. The compound of formula (1a) significantly reduces both paw lifting and paw licking, which occur during the late phase of the test. The advantage of the formula (1a) compound compared with milnacipran can be clearly seen when comparing the amplitude of the effects observed with a dose of 40 mg/Kg.

| Compound | Paw lifting Score observed at 40 mg/Kg | Paw licking Score observed at 40 mg/Kg |
| --- | --- | --- |
| 1a | 3.7 ± 1.1 | 1.0 ± 0.4 |
| milnacipran | 6.3 ± 1.4 | 2.0 ± 0.8 |

For both parameters, compound (1a) proves to be more effective than milnacipran, in particular with respect to paw lifting for which the difference with milnacipran is statistically significant.

To summarize, at a dose of 40 mg/Kg administered via intraperitoneal route (ip), compound (1a), representing the formula (1) compounds, produces higher analgesia than that produced by milnacipran in an acute pain model.

2) Evaluation of Antistress/Anxiolytic Activity:

Antistress/anxiolytic activity was determined on a conventional model using ultrasonic vocalizations (USVs) emitted by an adult rat when subjected to stress (Eur. J. Pharmacol. 2003, 463, 133).

Protocol:

The experiments were conducted in standard operative cages (250×320×250 mm) insulated from noise and light. The floor of the cages is covered with a grid in stainless steel and connected to an electric shock generator delivering a fixed intensity of 0.4 mA. The device is provided on one of its walls with a light source (2 lux). The ULTRAVOX system (Noldus, Wageningen, Pays Bas) is used to record ultrasonic vocalizations at a frequency defined by an ultrasound detector, an audio-filter box and acquisition software. For this experiment, the capture frequency was set at 22 kHz. The software allows the recording of all vocalizations of 22 kHz lasting a time of more 100 ms emitted by the animals. The test starts with a habituation session of 11 min 25 s, during which the animals are individually placed in the operative device without being subjected to conditioning (neither light nor electric shock).

During a second phase, the animals are subjected to a conditioning phase of 3 sessions given over 3 consecutive days. Each session consists of a pre-shock period of 160 s, followed by 15 repeats of conditioned stimulus (CS)/unconditioned stimulus (UCS); that is to say that an unavoidable shock of 0.4 mA (UCS) lasting 1 s is applied at the last second of light signal presentation (total time 5 s). Each CS/UCS pair is separated by an inter-test interval of 30 s. During the test phase, the same conditions are used as during the conditioning phase, with the difference that the electric shocks are not delivered 15 times. Here a single CS/UCS pair is applied at the start of a session, after a pre-shock period of 160 s. Next, only the light signal is maintained. The first test day is used to select those rats emitting USVs lasting 100 s or more (the animals which did not reach this laid-down criterion were therefore excluded from the study).

The selected rats are given a subcutaneous injection (volume 10 mL/kg) of physiological saline solution (control group) or the products to be tested. They are then isolated for 30 min before being placed in the operative cages for USV recording.

A rest period of 48 h is provided between each test (period for full elimination of the injected product).

Results:

In the USV test, the formula (1a) compound, representing this chemical series, and milnacipran have equivalent anti-stress/anxiolytic activity.

| Compound | Duration of USVs minimum significant dose (MSD mg/Kg) |
|---|---|
| 1a | 10 |
| milnacipran | 10 |

The minimum significant dose (MSD) needed to reduce the duration of the ultrasonic vocalizations is the same for both compounds. To summarize, compound (1a), representing compounds belonging to this chemical series, has antistress/anxiolytic properties that are as powerful as those of milnacipran after administering via intraperitoneal route.

3) Evaluation of Antidepressant Activity:

The antidepressant activity of the compounds of the invention was evidenced by the forced swimming test in rats (Eur. J. Pharmacol. 1978, 47, 379). This model is widely used since it is predictive of antidepressant activity in man.

Protocol:

The rats (Male Sprague Dawley rats (ICO: OFA SD [IOPS], Iffa Credo, France), are placed in a cylinder (height 45 cm and diameter 20 cm) filled with water at 25° C.±0.5 up to a height of 17 cm. This height allows the rats to swim or float without their paws touching the bottom of the cylinder. 24 h before the test day, the rats are placed in the cylinder for 15 min, after which time they no longer attempt to escape and remain immobile. On the test day, the animals are put back in the cylinder and the duration of immobility of the animal is measured and monitored using audiovisual recording for 5 min. The products of the invention are administered via ip route 30 min before the test. A rat is considered to be immobile when it allows itself to float and only makes small movements to remain on the surface.

Results:

The forced swim test (FIG. 1) shows that the formula (1a) compound, representing the series, is capable of significantly decreasing the duration of immobility of the animals at a dose of 40 mg/Kg after administering via ip route. By comparison, the same dose of milnacipran (40 mg/Kg) has no effect on the immobility of the animals under these test conditions. To summarize, compound (1a), and the compounds belonging to this chemical series, have anti-immobility properties representing antidepressant activity that are much higher than those of milnacipran, after a single administration.

The compounds of the invention therefore have a broad spectrum of activities i.e. anxiolytic, analgesic and antidepressant. The anti-immobility activity obtained after a single administration of the compounds of formula (1) is unexpected insofar as the monoamine reuptake inhibitors such as milnacipran or citalopram are only active under the conditions of this test after repeat administration. This characteristic of the compounds of formula (1) is advantageous since it could translate, in a depressed patient, as a reduction in the time of antidepressant action and/or improved response to treatment and hence the providing of a better medical service. In this respect, it is helpful to recall that the antidepressants that are currently clinically available are only effective after several weeks of treatment, and the percentage of responders to the treatment remains average (N. Engl. J. Med. 2006, 354, 1231; Lancet 2006, 367, 153).

The major antidepressant activity observed with the products of the invention could also be of advantage for the treatment of chronic pain. It is effectively acknowledged that in addition to the sensorial component (measured by acute pain tests) the emotional component plays an important role in chronic pain. Since the compounds of the invention act on both dimensions of pain (i.e.; sensorial and emotional) they could prove to be particularly well adapted for the treatment of chronic pain.

On this account, the compounds of general formula (1) or one of its therapeutically acceptable salts or one of its enantiomers are potentially useful as medicinal products, in particular in the treatment of some pathologies such as anxiety, depression the treatment of pain notably chronic pain, areas in which therapeutic needs are not entirely met and for which the discovery of new treatments is highly desirable.

The compounds of formula (1) or one of its therapeutically acceptable salts or one of its enantiomers can also be used for the treatment of fibromyalgia or erectile disorders such as early ejaculation or sexual impotence.

Pharmaceutical Composition:

A further subject of the invention concerns pharmaceutical compositions characterized in that, as active ingredient, they contain at least one formula (1) compound or an enantiomer or a pharmaceutically acceptable salt of a formula (1) compound associated with an inert pharmaceutical carrier or with other pharmaceutically acceptable vehicles.

The pharmaceutical compositions of the invention can, as an example, be compositions that can be administered by oral, nasal, sublingual, rectal or parenteral route. As examples of compositions which can be administered via oral route, mention may be made of tablets, capsules, granules, powders, solutions or oral suspensions. The suitable formulations for the chosen route of administration are known and described for example in: Remington, The Science and Practice of Pharmacy, 19$^{th}$ edition, 1995, Mack Publishing Company.

The efficient dose of a compound of the invention varies in relation to numerous parameters such as the chosen route of administration, the weight, age, gender, type of pathology and sensitivity of the individual to be treated. Consequently, the optimal dosage is to be determined in relation to parameters considered to be pertinent by a specialist in the area. Although the efficient doses of a compound of the invention may vary in large proportions, the daily doses could range from between 0.1 mg and 100 mg per Kg body weight of the person to be treated.

The administration of the compounds of the invention can be made via oral, nasal, sublingual, rectal or parenteral route. As non-limiting examples of formulation, a preparation of the compounds of the invention is described below. The ingredients and others which are therapeutically acceptable can be added in other proportions without modifying the scope of the invention. The term "active ingredient" refers to a compound of formula (1), one of its enantiomers or an addition salt with a pharmaceutically acceptable mineral acid or organic acid.

Formula to Prepare 1000 Tablets Each Containing 10 mg of Active Ingredient:

| | |
|---|---|
| Active ingredient | 10 g |
| Lactose | 100 g |

| Wheat starch | 10 g |
| Magnesium stearate | 3 g |
| Talc | 3 g |

The invention claimed is:

1. A compound of general formula (1)

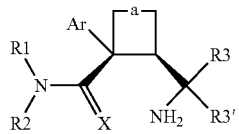

Formula 1 wherein:
-a- is a single or double bond,
Ar is an aromatic group, substituted or unsubstituted,
R1 and R2 each independently are: a hydrogen atom or a $C_1$-$C_6$ alkyl group, branched or unbranched, saturated or unsaturated, substituted or unsubstituted; R1 and R2 together may also form a heterocycle,
R3 and R3' each independently are a hydrogen atom or a $C_1$-$C_6$ alkyl group, and
X is an oxygen atom or a sulphur atom,
and the addition salts of the compounds of general formula (1) with pharmaceutically acceptable mineral acids or organic acids.

2. A compound of general formula (1) according to claim 1, wherein if Ar is substituted, the substituent(s) are: one or more halogen atoms, one or more $C_1$-$C_6$ alkyl groups, one or more $C_1$-$C_6$ alkoxy groups, or a cyano group.

3. A compound of general formula (1) according to claim 1, wherein if R1 and/or R2 is a substituted $C_1$-$C_6$ alkyl group, the substituent is: a halogen atom.

4. A compound of general formula (1) according to claim 1, wherein Ar is:
a phenyl group, unsubstituted or substituted by one or more halogen atoms, one or more $C_1$-$C_6$ alkyl groups, one or more $C_1$-$C_6$ alkoxy groups, or a cyano group,
or a naphthyl group, unsubstituted or substituted by one or more halogen atoms, one or more $C_1$-$C_6$ alkyl groups, one or more $C_1$-$C_6$ alkoxy groups, or a cyano group,
or a heteroaromatic group, unsubstituted or substituted by one or more halogen atoms, one or more $C_1$-$C_6$ alkyl groups, one or more $C_1$-$C_6$ alkoxy groups, or a cyano group.

5. A compound of general formula (1) according to claim 1, wherein Ar is:
a phenyl group, unsubstituted or substituted by one or two halogen atoms, one or two methyl groups, one or two methoxy groups, or a cyano group,
or a naphthylene group,
or a heteroaromatic group selected from the group consisting of: thiophene-2-yl, thiophen-3-yl and pyridin-3-yl.

6. A compound of general formula (1) according to claim 1, wherein R1 and R2 each independently are:
a $C_1$-$C_3$ alkyl group, branched or unbranched, saturated or unsaturated, optionally substituted by a fluorine atom,
or R1 and R2 together form a heterocycle selected from the group consisting of: pyrrolidine, indoline and tetrahydroisoquinoline.

7. A compound of general formula (1) according to claim 1, wherein R3 and R3' together represent a hydrogen atom or independently a methyl or ethyl group and a hydrogen atom.

8. A compound of general formula (1) according to claim 1, wherein X is an oxygen atom.

9. A compound of general formula (1) according to claim 1, selected from among:
cis-N,N-Diethyl-(1-phenyl-2-aminomethyl)-cyclobutanecarboxamide
cis-N,N-Diethyl-(1-phenyl-2-aminomethyl)-cyclobutenecarboxamide
cis-N,N-Diethyl-(1-(thiophen-2-yl)-2-aminomethyl)-cyclobutanecarboxamide
cis-N,N-Diethyl-(1-(thiophen-3-yl)-2-aminomethyl)-cyclobutanecarboxamide
cis-N,N-Diethyl-(1-(pyridin-3-yl)-2-aminomethyl)-cyclobutanecarboxamide
cis-N,N-Diethyl-(1-(naphthalen-2-yl)-2-aminomethyl)-cyclobutanecarboxamide
cis-N,N-Diethyl-(1-(2-fluorophenyl)-2-aminomethyl)-cyclobutanecarboxamide
cis-N,N-Diethyl-(1-(2-cyanophenyl)-2-aminomethyl)-cyclobutanecarboxamide
cis-N,N-Diethyl-(1-(3-chlorophenyl)-2-aminomethyl)-cyclobutanecarboxamide
cis-N,N-Diethyl-(1-(3-fluorophenyl)-2-aminomethyl)-cyclobutanecarboxamide
cis-N,N-Diethyl-(1-(3-methoxyphenyl)-2-aminomethyl)-cyclobutanecarboxamide
cis-N,N-Diethyl-(1-(3-cyanophenyl)-2-aminomethyl)-cyclobutanecarboxamide
cis-N,N-Diethyl-(1-(3-methylphenyl)-2-aminomethyl)-cyclobutanecarboxamide
cis-N,N-Diethyl-(1-(3,4-dichlorophenyl)-2-aminomethyl)-cyclobutanecarboxamide
cis-N,N-Diethyl-(1-(3,4-difluorophenyl)-2-aminomethyl)-cyclobutanecarboxamide
cis-N,N-Diethyl-(1-(3,4-methylenedioxyphenyl)-2-aminomethyl)-cyclobutanecarboxamide
cis-1-Indolin-1-yl-(1-phenyl-2-aminomethyl)-cyclobutanecarboxamide
cis-1-Indolin-1-yl-(1-(3-chlorophenyl)-2-aminomethyl)-cyclobutanecarboxamide
cis-1-Tetrahydroquinolin-2-yl-(1-phenyl-2-aminomethyl)-cyclobutanecarboxamide
cis-1-Tetrahydroquinolin-2-yl-(1-(3-fluorophenyl)-2-aminomethyl)-cyclobutanecarboxamide
cis-1-Tetrahydroquinolin-2-yl-(1-(3-chlorophenyl)-2-aminomethyl)-cyclobutanecarboxamide
cis-1-Tetrahydroquinolin-2-yl-(1-(3-cyanophenyl)-2-aminomethyl)-cyclobutanecarboxamide
cis-1-Tetrahydroquinolin-2-yl-(1-(3-methylphenyl)-2-aminomethyl)-cyclobutanecarboxamide
cis-N,N-Diallyl-(1-phenyl-2-aminomethyl)-cyclobutanecarboxamide
cis-N,N-Diallyl-(1-(3-fluorophenyl)-2-aminomethyl)-cyclobutanecarboxamide
cis-N,N-Diallyl-(1-(3-chlorophenyl)-2-aminomethyl)-cyclobutanecarboxamide
cis-N,N-Diallyl-2-yl-(1-(3-cyanophenyl)-2-aminomethyl)-cyclobutanecarboxamide
cis-N,N-Diallyl-2-yl-(1-(3-methylphenyl)-2-aminomethyl)-cyclobutanecarboxamide
cis-N,N-Diethyl-(1-phenyl-2-(1-aminoethyl))-cyclobutanecarboxamide
cis-N,N-Diethyl-(1-(3-chlorophenyl)-2-(1-aminoethyl))-cyclobutanecarboxamide and
cis-N,N-Diethyl-(1-phenyl-2-aminomethyl)-cyclobutanethiocarboxamide.

10. An enantiomer of a compound of formula (1) according to claim 1.

11. A method to prepare a compound of formula (1) according to claim 1, which comprises reacting an amine of formula R1R2NH with a compound of formula (4) to give a compound of formula (3); converting the compound of formula (3) to an azide of formula (2); and reducing the azide of formula (2) to produce the compound of formula (1) wherein (-a-), Ar, R1, R2, R3 and R3' are defined in claim 1, and wherein X is an oxygen atom, or if X is sulphur in formula (1), an additional step of protecting any primary amine groups followed by reaction with a thioanhydride wherein -a- is a single or double bond;
Ar is an aromatic group, substituted or unsubstituted;
R1 and R2 each independently are: a hydrogen atom or a $C_1$-$C_6$ alkyl group, branched or unbranched, saturated or unsaturated, substituted or unsubstituted; R1 and R2 together may also form a heterocycle, and
R3 and R3' each independently are a hydrogen atom or a $C_1$-$C_6$ alkyl group.

13. A compound of formula (3):

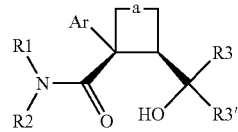

Formula 3 wherein
-a- is a single or double bond;
Ar is an aromatic group, substituted or unsubstituted;
R1 and R2 each independently are: a hydrogen atom or a $C_1$-$C_6$ alkyl group, branched or unbranched, saturated or unsaturated, substituted or unsubstituted; R1 and R2 together may also form a heterocycle, and
R3 and R3' each independently are a hydrogen atom or a $C_1$-$C_6$ alkyl group.

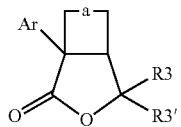

Formula 4

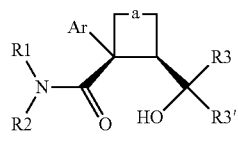

Formula 3

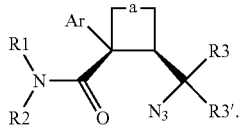

Formula 2

12. A compound of formula (2):

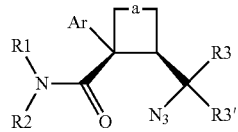

Formula 2

14. A method for the treatment of anxiety, which comprises administering to a patient in need thereof a compound of general formula (1) according to claim 1.

15. A method for the treatment of depression, which comprises administering to a patient in need thereof a compound of general formula (1) according to claim 1.

16. A method for the treatment of pain, which comprises administering to a patient in need thereof a compound of general formula (1) according to claim 1.

17. A pharmaceutical composition comprising at least one compound according to claim 1 or an enantiomer or a pharmaceutically acceptable salt thereof, and an inert pharmaceutical carrier or another pharmaceutically acceptable vehicle.

* * * * *

UNITED STATES PATENT AND TRADEMARK OFFICE
CERTIFICATE OF CORRECTION

PATENT NO. : 8,455,550 B2
APPLICATION NO. : 13/258546
DATED : June 4, 2013
INVENTOR(S) : Cuisiat et al.

It is certified that error appears in the above-identified patent and that said Letters Patent is hereby corrected as shown below:

ON THE TITLE PAGE:
Item [75], Inventors, change "Olivier Vitton, Castres (FR)" to --Olivier Vitton, Lempaut (FR)--.

IN THE SPECIFICATION:

Column 7, line 55, Example 1, change "$C_{26}H_{24}N_2O$" to --$C_{16}H_{24}N_2O$--; line 66, Example 1, change "$C_{26}H_{24}N_2O.C_2H_2O_4$" to --$C_{16}H_{24}N_2O.C_2H_2O_4$--.

Column 9, line 66, Example 6, change "$C_{24}H_{20}N_2O.C_2H_2O_2$" to --$C_{14}H_{20}N_2O.C_2H_2O_2$--.

Column 10, line 19, Example 7, change "$C_{28}H_{24}N_2O.C_4H_4O_4$" to --$C_{18}H_{24}N_2O.C_4H_4O_4$--; line 41, Example 8, change "$C_{24}H_{22}N_2OS.C_4H_4O_4$" to --$C_{14}H_{22}N_2OS.C_4H_4O_4$--; and line 60, Example 9, change "$C_{24}H_{22}N_2OS.C_4H_4O_4$" to --$C_{14}H_{22}N_2OS.C_4H_4O_4$--.

Column 11, line 11, Example 10, change "$C_{26}H_{23}ClN_2O.C_4H_4O_4$" to --$C_{16}H_{23}ClN_2O.C_4H_4O_4$--; line 24, in Example 11, after "hyl))-cyclobutanecarboxamide", insert --(1i)--; line 31, Example 11, change "$C_{26}H_{23}ClN_2O.C_4H_4O_4$" to --$C_{16}H_{23}ClN_2O.C_4H_4O_4$--; and line 51, Example 12, change "$C_{26}H_{23}FN_2O.C_8H_8O_8$" to --$C_{16}H_{23}FN_2O.C_8H_8O_8$--.

Column 12, line 4, Example 13, change "$C_{26}H_{22}Cl_2N_2O.C_4H_4O_4$" to --$C_{16}H_{22}Cl_2N_2O.C_4H_4O_4$--; line 24, Example 14, change "$C_{26}H_{22}Cl_2N_2O.C_4H_4O_4$" to --$C_{16}H_{22}Cl_2N_2O.C_4H_4O_4$--; line 44, Example 15, change "$C_{27}H_{26}N_2O_2.C_4H_4O_4$" to --$C_{17}H_{26}N_2O_2.C_4H_4O_4$--; and line 64, Example 16, change "$C_{27}H_{24}N_2O_3.C_4H_4O_4$" to --$C_{17}H_{24}N_2O_3.C_4H_4O_4$--.

Column 13, line 10, Example 17, after "cyclobutanecarboxamide", insert --(1o)--; line 17, Example 17, change "$C_{27}H_{26}N_2O.C_4H_4O_4$" to --$C_{17}H_{26}N_2O.C_4H_4O_4$--.

Signed and Sealed this
Twenty-third Day of September, 2014

Michelle K. Lee
*Deputy Director of the United States Patent and Trademark Office*